US006667091B1

(12) United States Patent
Castro Netto

(10) Patent No.: US 6,667,091 B1
(45) Date of Patent: Dec. 23, 2003

(54) INJECTED PLASTIC PRODUCT WITH INDIVIDUALIZED IDENTIFICATION AND INJECTION MOULD FOR MANUFACTURING THE PRODUCT

(75) Inventor: Eduardo De Lima Castro Netto, deceased, late of Rio de Janeiro (BR), by Lydia de Faria Lima Castro, executor

(73) Assignee: ELC Produtos de Seguranca Industria e Comerico Ltda., Rio de Janeiro (BR)

( * ) Notice: Subject to any disclaimer, the term of this patent is extended or adjusted under 35 U.S.C. 154(b) by 0 days.

(21) Appl. No.: 09/491,043

(22) Filed: Jan. 25, 2000

(30) Foreign Application Priority Data

Jan. 25, 1999 (BR) .......................................... 9900304
Oct. 11, 1999 (BR) .......................................... 9905095

(51) Int. Cl.[7] .......................... B32B 3/00; A61B 5/117; D06N 7/04; G09F 3/14; B42D 15/00

(52) U.S. Cl. ...................... 428/161; 428/141; 428/142; 428/172; 283/72; 283/105; 283/107; 24/17 AP; 24/16 PB; 24/30.5 P; 40/633; 40/665; 40/625; 292/307 R

(58) Field of Search .......................... 24/30.5 P, 17 AP, 24/16 PB; 428/141, 142, 172, 161; 283/72–114; 292/307 R, 318, 317; 40/21 C, 633, 665, 632, 625

(56) References Cited

U.S. PATENT DOCUMENTS

| | | | | | |
|---|---|---|---|---|---|
| 2,911,743 | A | * | 11/1959 | Pokras | 40/633 |
| 3,106,028 | A | * | 10/1963 | Baumgartner | 40/21 |
| 3,197,899 | A | * | 8/1965 | Twentier | 40/633 |
| 4,078,324 | A | * | 3/1978 | Wiebe | 40/665 |
| 4,272,900 | A | * | 6/1981 | MacLarty et al. | 40/21 |
| 4,285,146 | A | * | 8/1981 | Charles et al. | 40/665 |
| 4,506,415 | A | * | 3/1985 | Swift | 24/16 |
| 4,537,432 | A | * | 8/1985 | Meeks | 292/318 |
| 4,914,843 | A | * | 4/1990 | DeWoskin | 40/633 |
| 5,542,724 | A | * | 8/1996 | Netto | 292/317 |
| 5,765,885 | A | * | 6/1998 | Netto | 292/318 |

* cited by examiner

*Primary Examiner*—Sandra M. Nolan
*Assistant Examiner*—Catherine A. Simone
(74) *Attorney, Agent, or Firm*—Smith, Gambrell & Russell, LLP

(57) ABSTRACT

An injected plastic product, such as a security seal, individualised by means of a strip of paper printed with an identification and integrated with an identification surface of the product. According to the invention, delamination of the strip of paper, so as to remove the outer layer or layers with the individualized identification, is not possible without tearing the paper. This may be done by forming the identification surface with one or more small protuberances which are covered by the paper strip or by at least part of the outer surface of the paper strip covered by the plastic injected when making the product. Injection molds suitable for making the product are also disclosed.

16 Claims, 8 Drawing Sheets

INJECTED PLASTIC PRODUCT WITH INDIVIDUALIZED IDENTIFICATION AND INJECTION MOULD FOR MANUFACTURING THE PRODUCT

FIELD OF THE INVENTION

The present invention refers to a plastic product and especially to a security seal with individualized identification and to an injection mold for manufacturing the product.

The product to which this invention refers is of the plastic injection molded type having an identification surface to which an individualized marking is applied, such as a number, bar code or the like.

PRIOR ART

One of the essential requirements for a security seal to have a high degree of security is that it is individualized so as to prevent its substitution by another identical seal. One of the safest ways of effecting such individualization is by means of numbering in high relief during injection of the plastic from which the seal is made. This solution, however, is relatively costly in view of the resultant complexity of the mold and of the maintenance thereof.

A less costly technique is to adhere a strip of paper to the identification surface, on which a number or other marking which serves to distinguish the seal from otherwise identical seals is printed. Mere adhesion, however, does not provide a high degree of security in view of the possibility of removing the printed strip from a tampered seals and later applying it to another seal. This process may be made more difficult and there are various ways of doing this, but the danger of the strip being removed and re-utilized is always present.

Another manner of applying a personalized strip of paper is to apply it at the time of injecting the plastic so that the strip becomes integral with the seal at the time of manufacture. Although this technique does have excellent results and is considerably superior to simple gluing, all papers have a laminated structure and this permits a violator to delaminate the strip, removing the upper layer or layers with the number printed thereon and leaving only the lowermost layer on the tampered seal. The removed strip can then be glued onto a new seal, making it difficult to identify the violation.

OBJECTS OF THE INVENTION

A first object of the present invention is to individualize a plastic product, such as a security seal of the type mentioned above, using a printed strip of paper fixed to an identification surface, at low cost and without compromising the desired high degree of security provided.

Another object of the invention is to provide an injection mold for manufacturing the product.

GENERIC DEFINITION OF THE INVENTION

According to a first aspect of the present invention, a product made from injected plastic and having an identification surface to which a strip of paper printed with an individualized identification is fixed, is characterized in that at least part of the identification surface has at least one protuberance covered by the strip of paper, to define at least one abrupt change in the plane of part of the outer surface of the strip of paper.

A product having such a characteristic will not permit the removal of the complete outer face of the strip of paper without tearing. Consequently, if the part removed by a violator is glued to another similar product, it will always be incomplete or damaged, leaving clear vestiges of adulteration.

In the preferred embodiments of this invention, there are various protuberances on the identification surface, which may take the form of square or rectangular protuberances, small pins, small tooth-like formations or the like. The important feature is that the outer or exposed surface of the strip of paper has portions the plane of which changes abruptly along crease lines, edges or the like, such abrupt changes in direction of the surface of the paper adhered to the identification surface favoring the formation of tear regions in the eventuality of an attempt at removal.

According to a second aspect of the present invention, a product made from injected plastic and having an identification surface to which a strip of paper printed with an individualized identification is fixed, is characterized in that at least part of the outer surface of the strip of paper is covered by the injected plastic of the product.

As in the first aspect of the invention as mentioned above, such a characteristic will not permit the removal of the complete outer face of the strip of paper without tearing.

In a preferred embodiment of the second aspect of the invention, it has been found that a particularly practical manner of making the injected plastic pass to the outer surface of the strip of paper is by the partial perforation of the paper in the corresponding region.

The invention also relates to an injection mold for manufacturing a plastic product with individualized identification, which comprises first and second injection mold halves, the first mold half being formed with an injection cavity for forming part of the product to be personalized by solidifying the injected plastic with a printed strip of paper placed between the mold halves, and the second mold half closing the cavity in a closed configuration of the mold with the halves in mutual contact.

In the case of a mold for manufacturing a product in accordance with the first aspect of the invention, as mentioned above, small reentrances are formed in the second mold half so as to permit that, at the time of injection of the plastic in the closed configuration of the mold, the plastic under pressure in the injection cavity deforms small regions of the strip of paper, forcing them into the small reentrances.

Preferably, there are two series of the small reentrances in the second mold half, located at positions corresponding to two opposite sides of the injection cavity. Each small reentrance may have a constant rectangular cross section, parallel to the surface of the second mold half.

In the case of a mold for manufacturing a product in accordance with the second aspect of the invention, as mentioned above, the second mold half is shaped so as to permit, at the time of injection of the plastic in the closed configuration of the mold, the plastic at least partially covers the side of the strip of paper that is remote from the mold cavity.

In this case it is preferred that there are two roughened regions located at positions corresponding to two opposite sides of the injection cavity. Each of these roughened regions may extend completely along the respective side of the cavity, in the closed configuration of the mold. Furthermore, there can be four roughened regions located at positions, in the closed configuration of the mold, corresponding to the four corners of the cavity.

BRIEF DESCRIPTION OF THE DRAWINGS

The present invention will be better understood from the following description, given by way of example, reference being made to the drawings, in which.

DETAILED DESCRIPTION OF THE DRAWINGS

Figure 1:
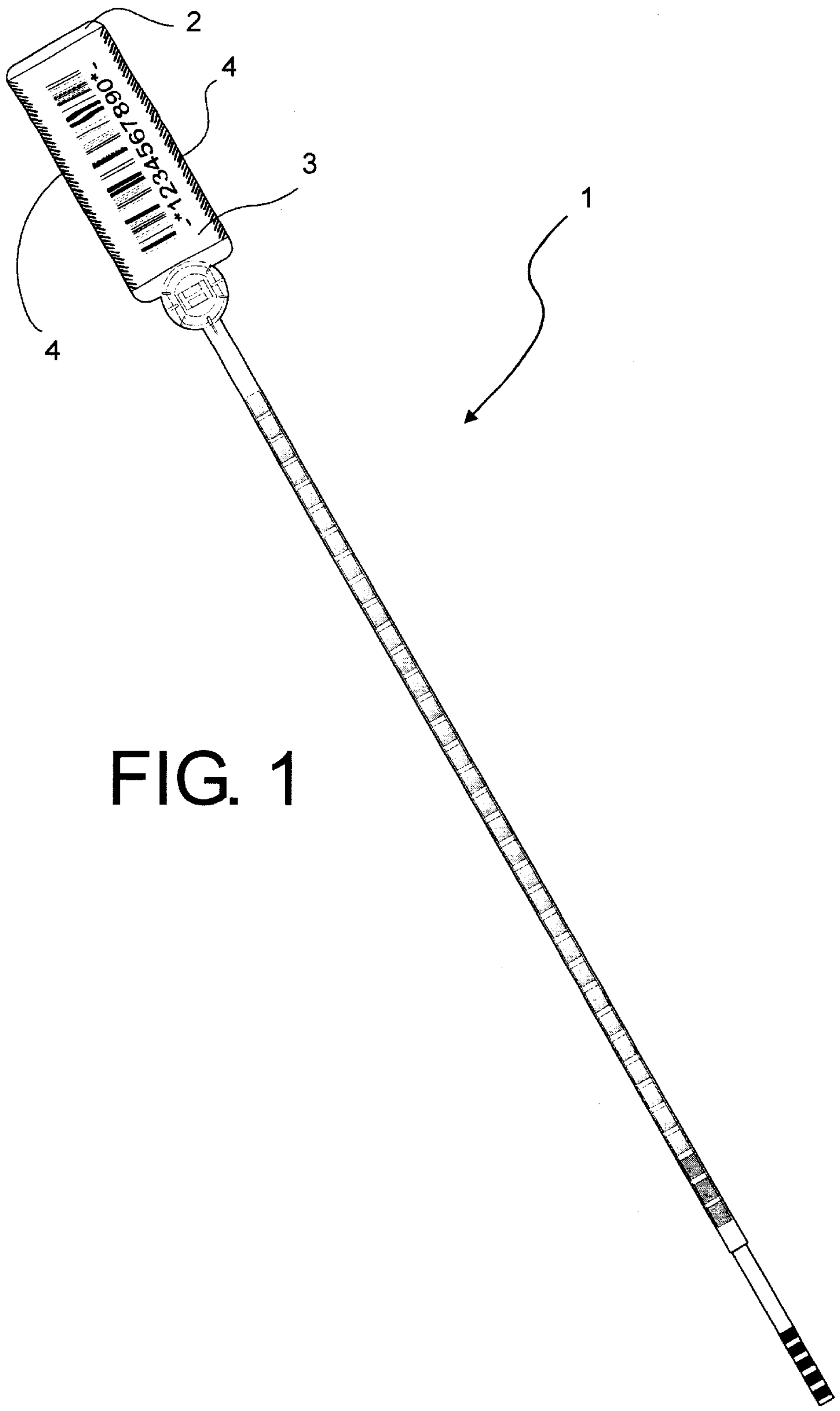
FIG. 1 is a perspective view of a security seal having fixed thereto a strip of paper printed with an identification number, according to a first preferred embodiment of the invention.

Referring now to FIG. 1 of the drawings, a first preferred embodiment of the present invention is shown as a plastic injected security seal 1 having a tab or blade 2 defining an identification surface. A strip of paper 3 printed with an identification number is fixed to the identification surface. It should be noted that the printing on strip 3 may be any type of individualization, be it a number as illustrated, a bar code, or both, or any other sign that serves to distinguish the seal from any other similar seal.

The strip of paper 3 has been fixed to the seal at the time of injection of the plastic of which the seal is made, so that its lower surface has become integral with the plastic of the seal. In this respect the illustrated seal is identical to the known seals mentioned in the introduction to this specification.

According to a first preferred embodiment of this invention, however, adjacent one of the side edges 4 of the strip of paper 3, there are two series of four small rectangular protuberances 4*a*, all correspondingly aligned with each other. Each protuberance has a constant rectangular cross section, in all planes parallel to the surface of blade 2. The protuberances are dimensioned so as to be perfectly covered by the paper of strip 3, by means of deformation of the paper, without any tearing, at the time of injection of the seal.

The fact that blade 2, including its protuberances 4*a*, is totally covered by the strip of paper 3 during injection, results in a true incorporation or integration of edges 4 at the lower surface of strip 3 with the material of the seal. This completely prevents removal of the strip or even of its upper layer or layers without at least tearing the paper in the region of the protuberances.

Although the seal illustrated in FIG. 1 has its protuberances 4*a* parallel and adjacent to one of the opposite edges 4 of strip 3, the protuberances could be formed at any location on the surface of the blade 2 and there could be any number of them. The shape of the protuberances could also be varied. For example, they could be cylindrical or triangular. The essential feature is that the alterations in the planes of the surface of the paper in the region of the protuberances must be abrupt due to the existance of edges or corners, which makes it impossible to remove the paper without tearing.

Furthermore, although the invention is especially appropriate for use in individualizing security seals, it could be used with any injected plastic product which is desired to be marked with total security.

FIGS. 2 to 6 show diagrammatically an injection mold adapted to manufacture individualized products in accordance with the present invention, and more particularly having the characteristics of the seal illustrated in FIG. 1. The injection mold is comprised of two mold plates or halves 5 and 6. Mold half 5 is formed with four injection cavities 7 in which the identification portions (for example, the blade 2 in the case of the seal of FIG. 1) of four products to be injection molded are to be formed. It is to be observed that the complete cavities where the other parts of the products are to be formed are not shown in FIGS. 2 to 6, it being sufficient for an understanding of the invention to see the cavities where the portions to be identified by means of the printed paper are to be formed.

The two mold plates or halves are also provided with complementary cavities 8 and 9 which define the flow channels for the plastic to be injected into cavities 7, whereas the actual injection channel 10 can be seen in plate 5.

Plate 6 is also formed with four pairs of small rectangular reentrances 11 which correspond to the protuberances 4*a* of FIG. 1, in suitable positions opposite cavities 7 in plate 5.

Figure 2:
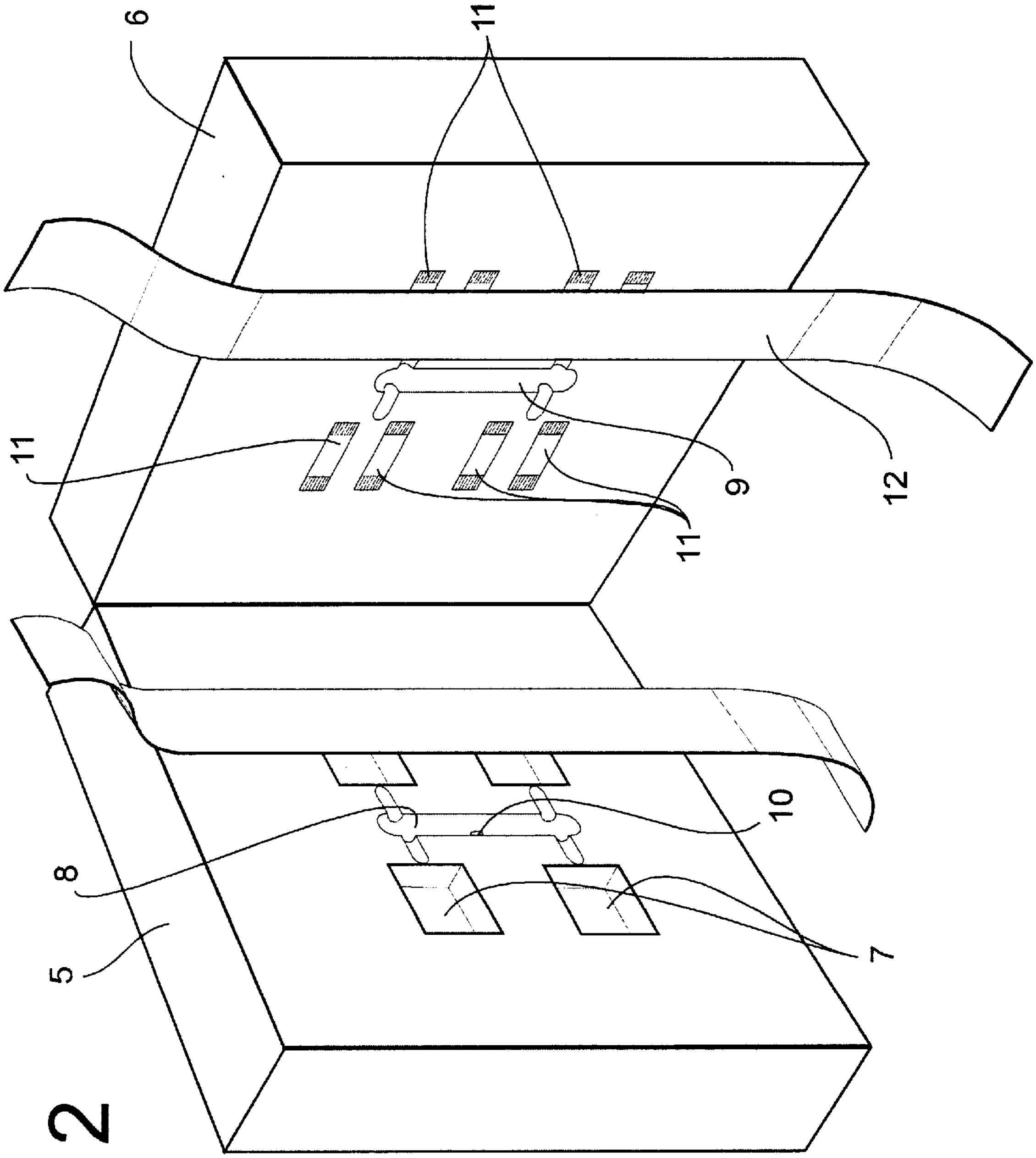
FIG. 2 is a diagrammatic representation, in perspective, of two mold halves of a first embodiment of an injection mold according to the present invention, of a type suitable for use in manufacturing the seal of FIG. 1.
Figure 3:
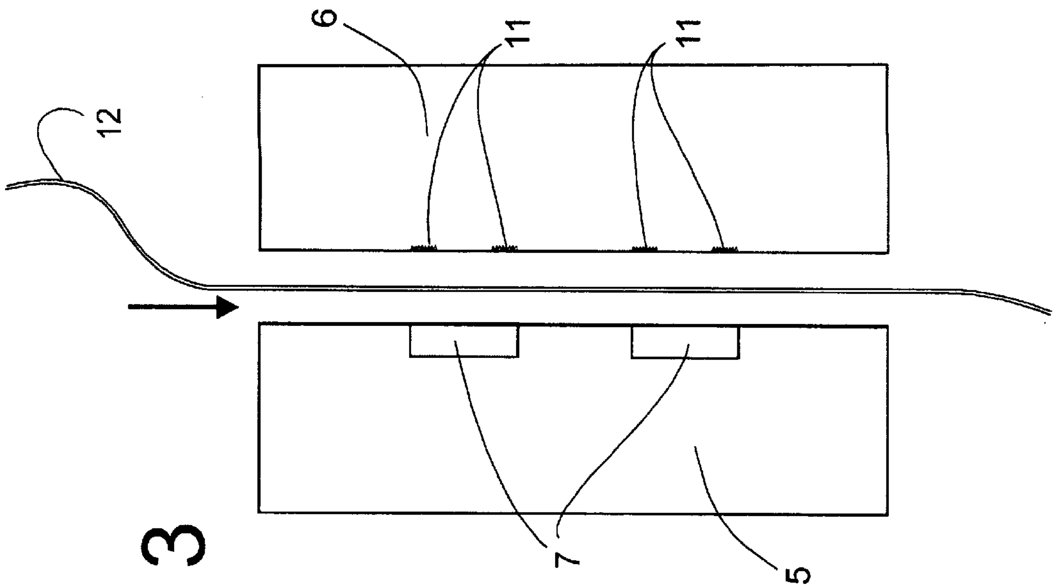
FIG. 3 is a side view of the mold halves shown in FIG. 2, prior to closing of the mold, shortly prior to injection.

FIG. 2 also shows two continuous strips of paper 12 that run in parallel along the faces of plates 5 and 6. The surfaces of strips 12 carry a series of printed numbers that serve to provide the individualized identification of each product to be formed in cavities 7. The arrangement is best seen in FIG. 3 which shows plates 5 and 6 in the mold open position, with the continuous paper strips 12 (only one of the strips being shown in this figure) passing on the one hand in front of injection cavities 7 and, on the other, in front of the small reentrances in plate 6.

Figure 4:
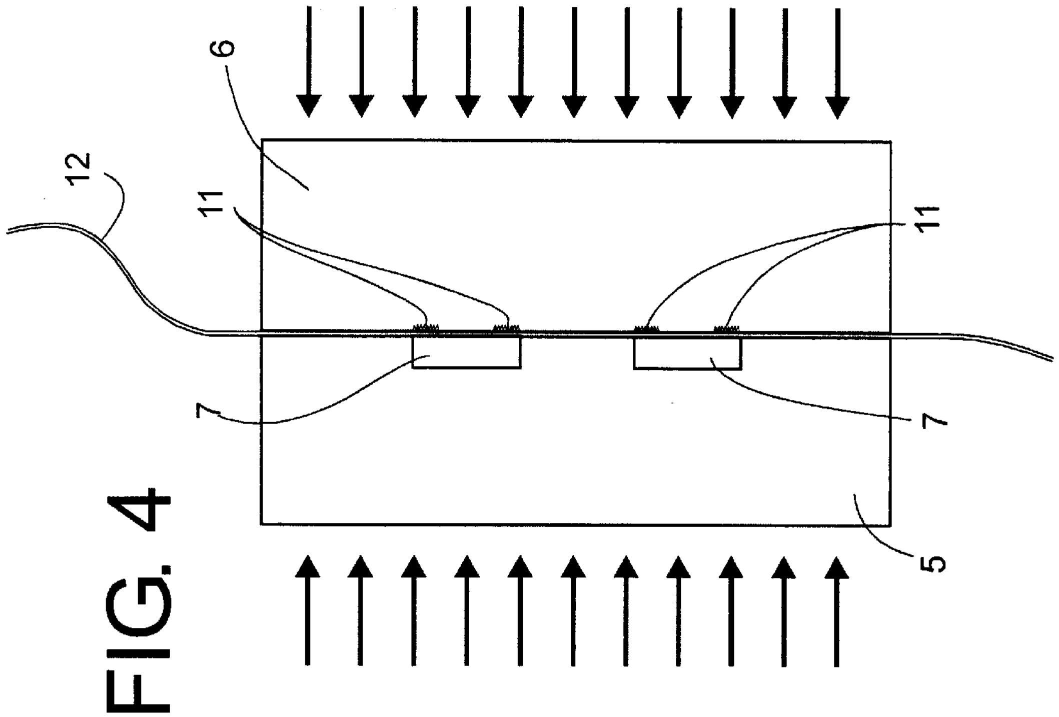
FIG. 4 is a side view of the closed mold of FIGS. 2 and 3, at the time of injection.
Figure 5:
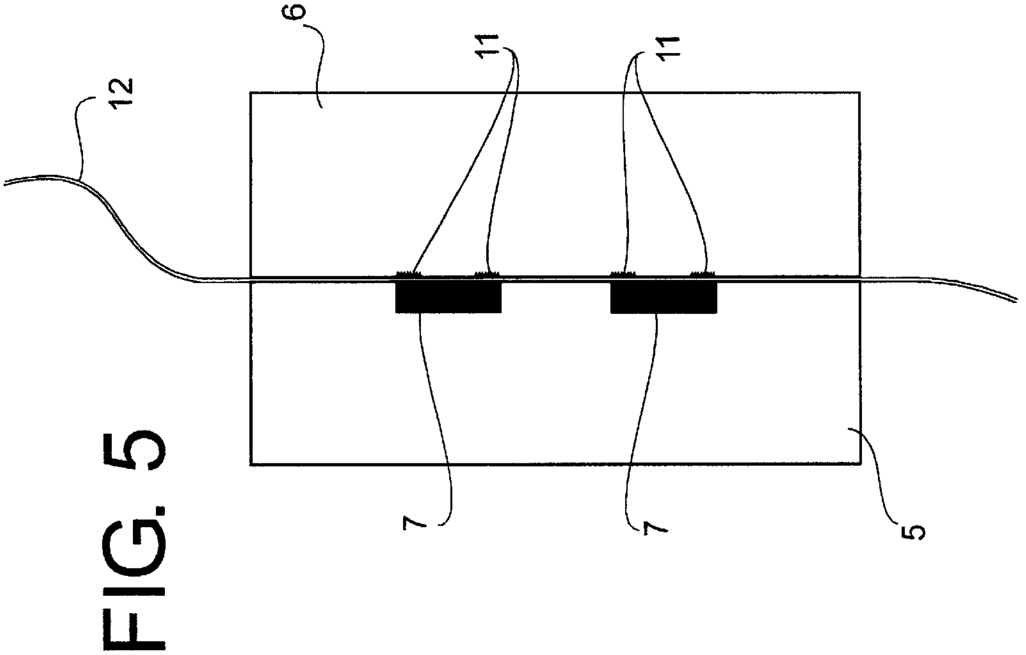
FIG. 5 is a view similar to FIG. 4, indicating the plastic injected into the mold and the fixing of the strip of paper at the time of injection.
Figure 6:
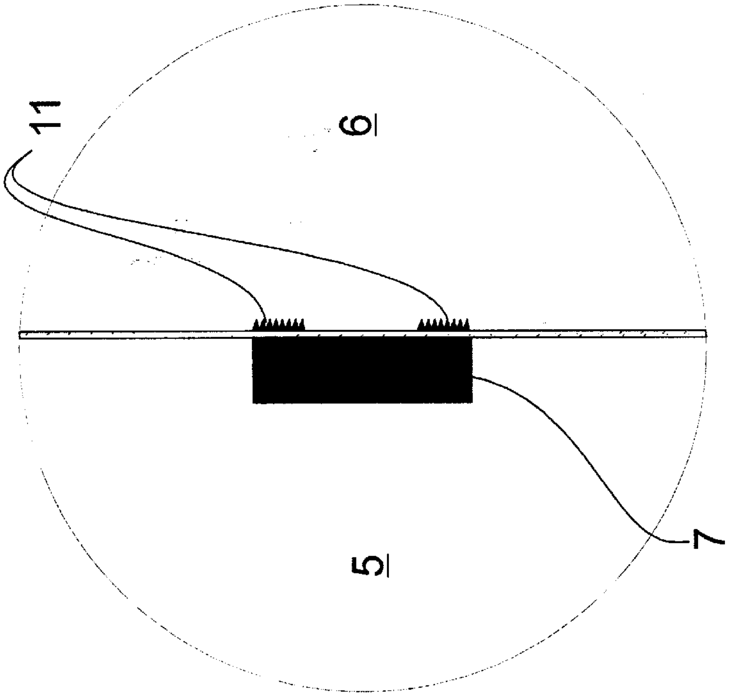
FIG. 6 is a detail of FIG. 5.

The mold is then closed, as shown in FIG. 4, at which instant plastic is injected through injection channel 10 and along the flow channels formed by cavities 8 and 9 in the two plates 5 and 6, to be applied under high pressure to the interior of cavities 7. As the cavities fill with the molten plastic, the plastic pressures the continuous strips of paper 12 in the regions where they pass over cavities 7, strongly forcing the paper 12 against plate 6 and deforming it into the small reentrances 11, without, however, tearing the paper (see FIGS. 5 and 6).

Continued injection pressure results in the plastic completely filling cavities 7 until injection is terminated.

Mold plates or halves 5 and 6 are then separated and demolding is effected, the products molded in cavities 7 then being removed together, connected in series by means of the continuous strips of paper 12. The individual products can then be separated from each other by cutting the paper along the edges of the products that correspond to the edges of cavities 7.

The product thus formed will have a short strip of duly numbered paper integrated with the body of the product over its entire inner or lower face. As previously explained, even if it were to be possible to remove the main portion of one of the small strips, or the outer layer of one of them, by careful delamination of the paper, the paper would be torn in the regions of the protuberances formed in the reentrances 11 of the mold.

Also as mentioned above, reentrances 11 could be located at any position on mold plate 6 that is superimposed, in the closed configuration of the mold, on the respective cavities 7, it being possible to have just one reentrance or a plurality of them associated with each cavity.

Figure 7:
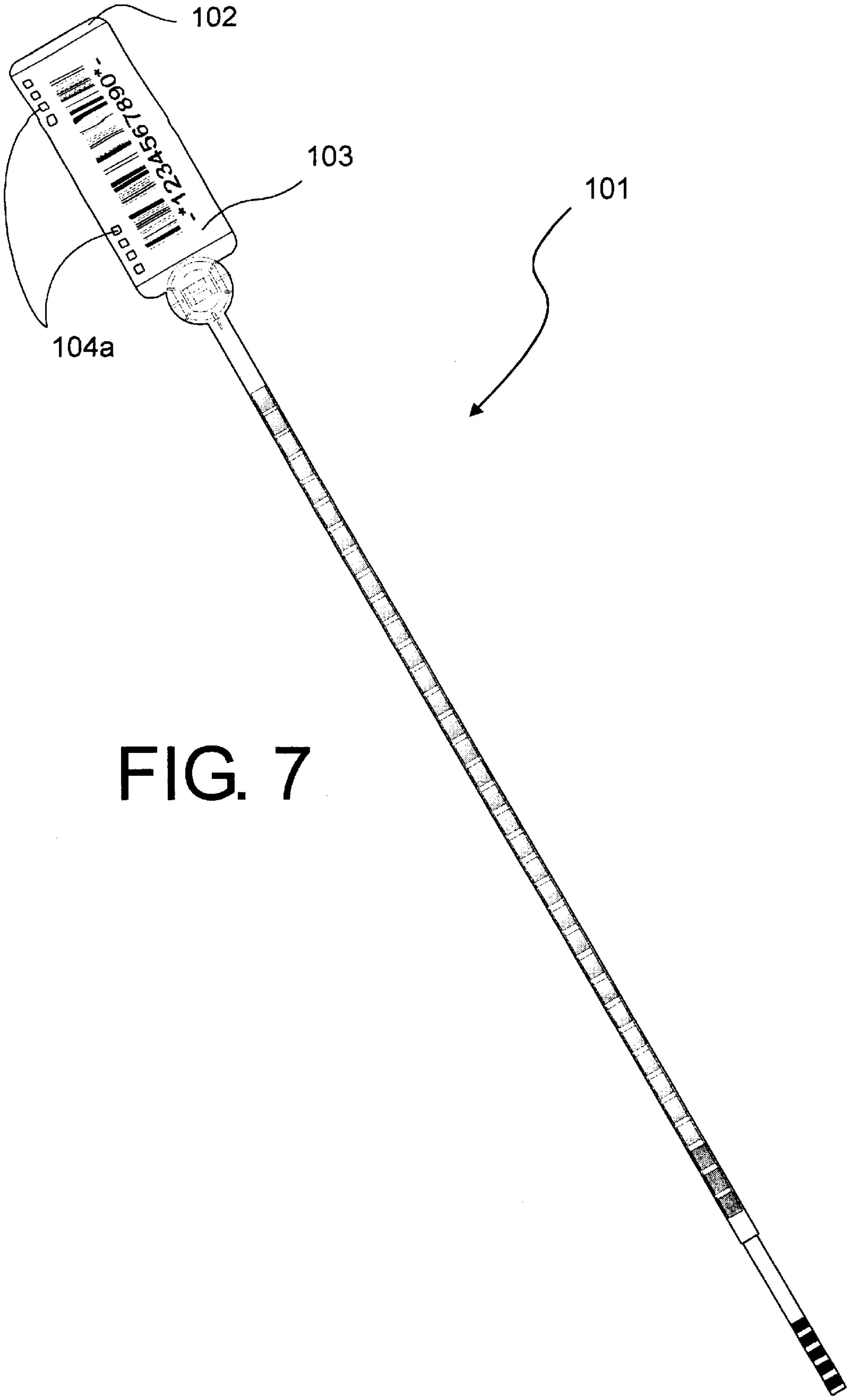
FIG. 7 is a perspective view of a security seal having fixed thereto a strip of paper printed with an identification number, according to a second preferred embodiment of the invention.

Referring now to FIG. 7 of the drawings, which is generally similar to FIG. 1, another preferred embodiment is shown, in accordance with the second aspect of the invention. FIG. 7 shows a plastic injected security seal 101 having a tab or blade 102 defining an identification surface. A strip of paper 103 printed with an identification number is fixed to the identification surface. It should be noted that the printing on strip 103 may be any type of individualization, be it a number as illustrated, a bar code, or both, or any other sign that serves to distinguish the seal from any other similar seal.

The strip of paper 103 has been fixed to the seal 101 at the time of injection of the plastic of which the seal is made, so that its lower surface has become integral with the plastic of the seal. In this respect the illustrated seal is identical to the known seals mentioned in the introduction to this specification. In accordance with this second preferred embodiment, however, the side edges 104 of the paper strip 103 are partially covered by the plastic of the seal, such covering having been created during the injection of the seal.

It will be seen that side edges 104 of the strip are not totally covered by the plastic, there being small regions where the paper is visible. This is due to the fact that, as will become clear later, at the time of injection of the seal the edges 104 of the paper strip are perforated by the pressurised plastic being injected, the plastic flowing only partially over the outer surface of the paper, thus truly incorporating the edges 104 in the material of the seal. This makes it absolutely impossible to remove the paper strip or even the outer layer or layers thereof without tearing the paper at least in the region of its edges.

Although seal 101 shown in FIG. 1 has its two opposite edges 104 covered or partially covered by the plastic along their entire extension, a similar effect can be obtained if the covering were to be only partially along one or both of the edges, if it were only to exist at the corners or even if it were to be in one or more regions remote from the edges. The important point is that at least part of the paper of strip 103 is covered by plastic during the injection of the seal so that that part or those parts become inseparable from blade 102 of the seal.

FIGS. 8 to 12 show diagrammatically an injection mold adapted to manufacture individualized products in accordance with the second aspect of the present invention, and more particularly having the characteristics of the seal illustrated in FIG. 7. Similar to the mold illustrated in FIG. 2 to 6, the injection mold is comprised of two mold plates or halves 105 and 106. Mold half 105 is formed with four injection cavities 107 in which the identification portions (for example, the blade 12 in the case of the seal of FIG. 7) of four products to be injection molded are to be formed. It is to be observed that the complete cavities where the other parts of the products are to be formed are not shown in FIGS. 8 to 12, it being sufficient for an understanding of this aspect of the invention to see the cavities where the portions to be identified by means of the printed paper are to be formed.

The two mold plates or halves 105 and 106 are also provided with complementary cavities 108 and 109 which define the flow channels for the plastic to be injected into cavities 107, whereas the actual injection channel 110 can be seen in plate 105.

Plate 106 is also formed with four pairs of rectangular regions 111 having a saw tooth like configuration, the saw teeth of each pair being parallel to each other. Each saw tooth region is located at a position corresponding to one edge of one of the cavities 107 in plate 105 so that, when the plates are closed against each other, it runs along the inner side of the edge of the cavity.

Figure 8:
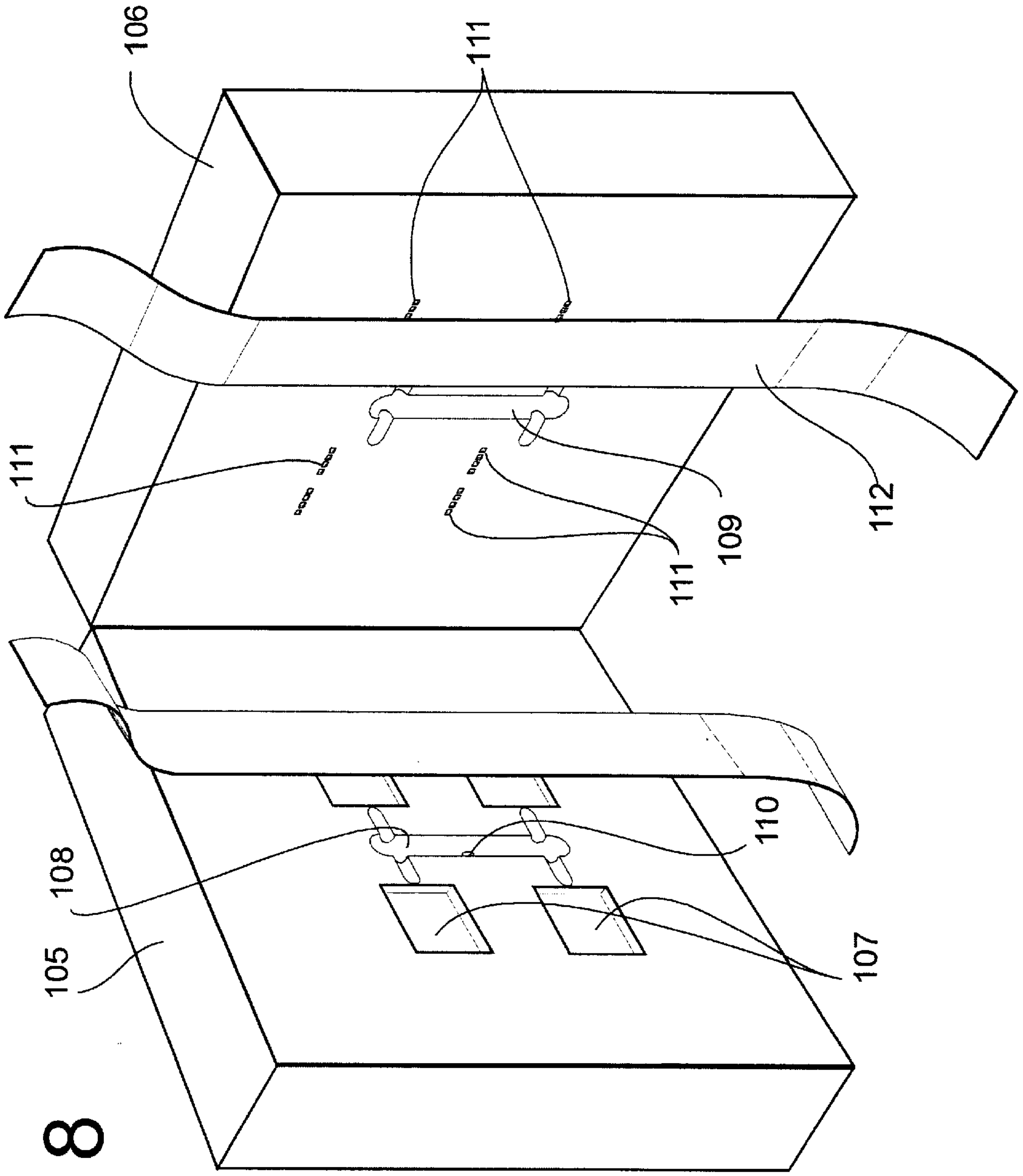
FIG. 8. is a diagrammatic representation, in perspective, of two mold halves of a second embodiment of an injection mold according to the present invention, of a type suitable for use in manufacturing the seal of FIG. 7.
Figure 9:
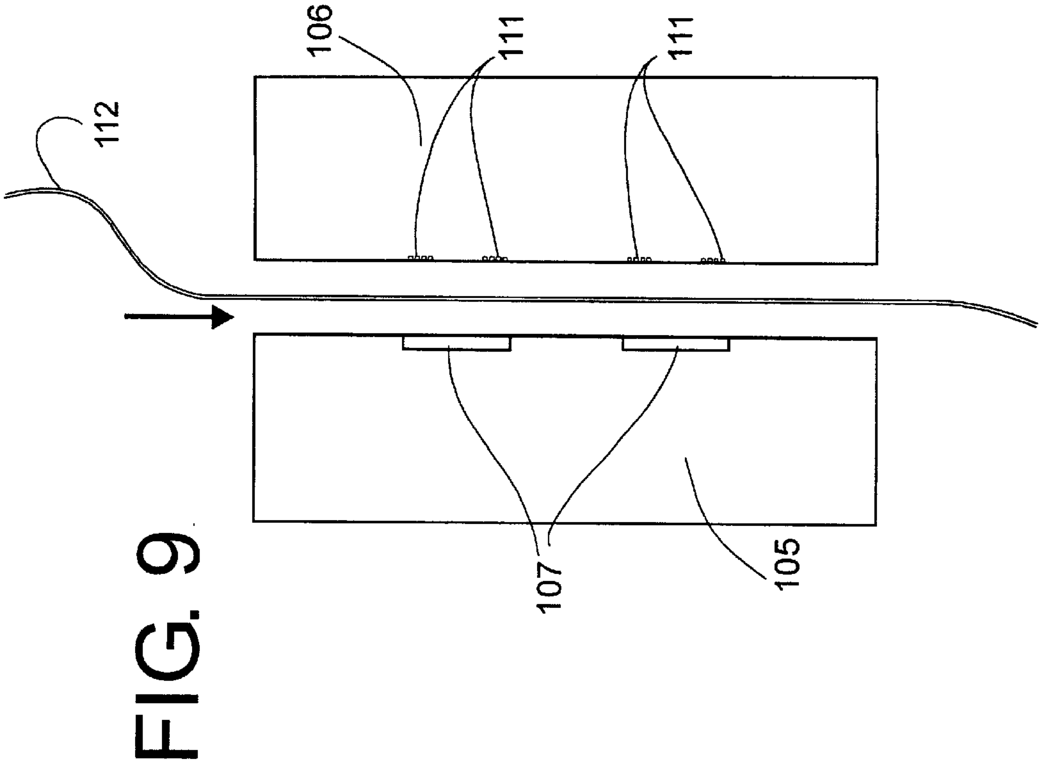
FIG. 9 is a side view of the mold halves shown in FIG. 8, prior to closing of the mold, shortly prior to injection.

FIG. 8 also shows two continuous strips of paper 112 that run in parallel along the faces of plates 105 and 106. The surfaces of strips 112 facing plate 106 carry a series of printed numbers that serve to provide the individualized identification of each product to be formed in cavities 107. The arrangement is best seen in FIG. 9 which shows plates 105 and 106 in the mold open position, with the continuous paper strips 12 (only one of the strips being shown in this figure) adjacent the face of plate 106, its side edges passing over the saw tooth regions 111.

Figure 10:
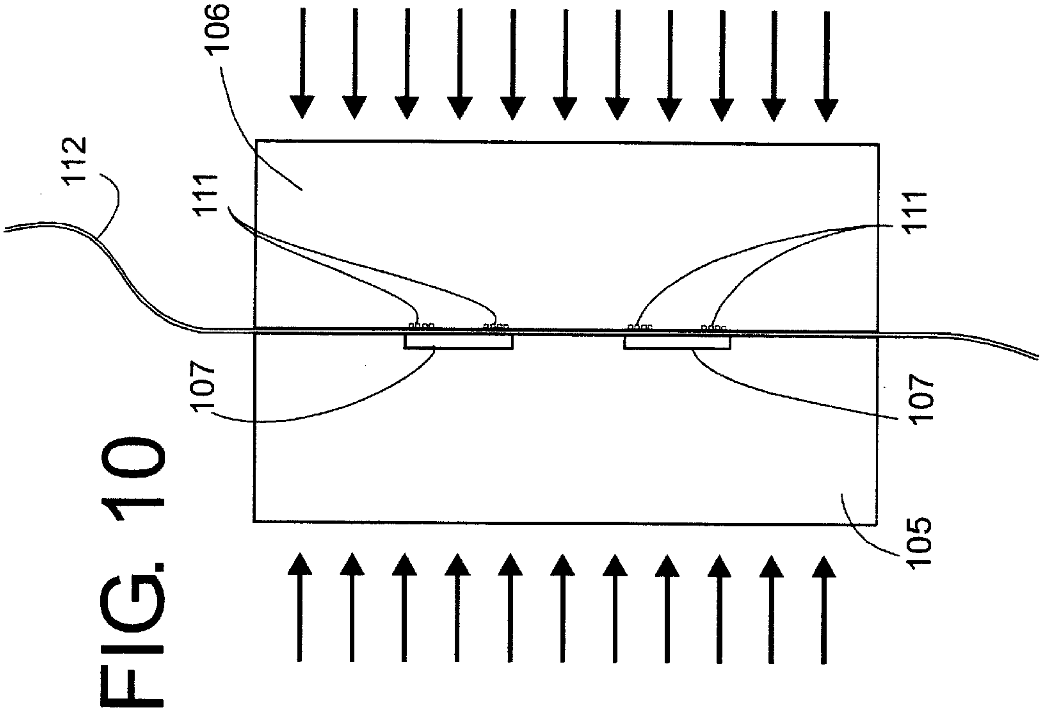
FIG. 10 is a side view of the closed mold of FIGS. and 9, at the time of injection.
Figure 11:
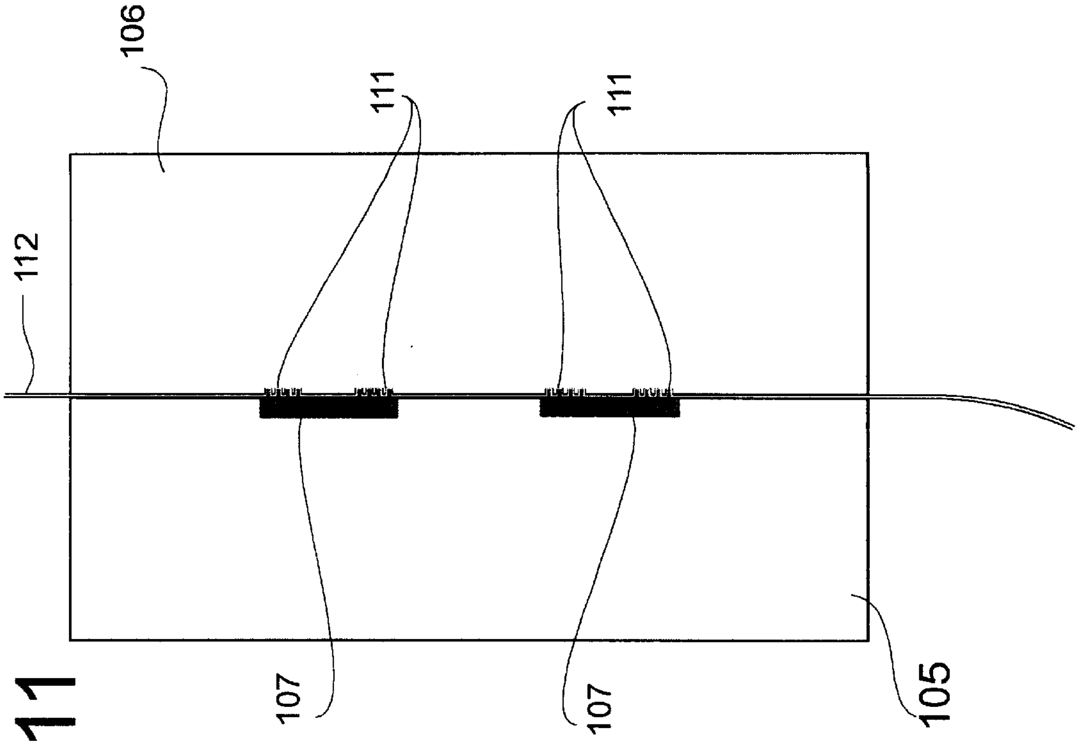
FIG. 11 is a view similar to FIG. 10, indicating the plastic injected into the mold and the fixing of the strip of paper at the time of injection.
Figure 12:
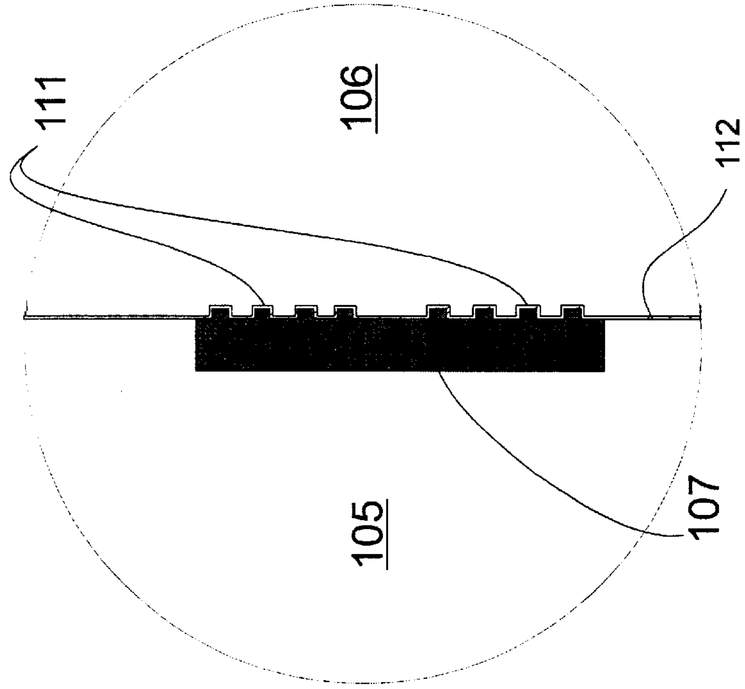
FIG. 12 is a detail of FIG. 11.

The mold is then closed, as shown in FIG. 10 at which instant plastic is injected through injection channel 110 in plate 105 and along the flow channels formed by cavities 108 and 109 in the two plates 105 and 106, to be applied under high pressure to the interior of cavities 107. As the cavities fill with the molten plastic, the plastic pressures the continuous strips of paper 112 in the regions where they pass over cavities 117, strongly forcing the paper 12 against plate 6 the saw tooth regions 111. This has the effect of perforating the paper in the inner parts of the saw tooth regions and the plastic then passes through the perforations thus formed, passing to the other side of the paper and partially covering it (see FIGS. 11 and 12).

Continued injection pressure results in the plastic completely filling cavities 7 until injection is terminated.

Mold plates or halves 105 and 106 are then separated and demolding is effected, the products molded in cavities 107 then being removed together, connected in series by means of the continuous strips of paper 112. The individual products can then be separated from each other by cutting the paper along the outer edges of the regions that correspond to the saw tooth regions 111 on the mold.

The product thus formed will have a short strip of duly numbered paper integrated with the body of the product over its entire inner or lower face and, furthermore, over its inner and outer surfaces at its side edges that correspond to the saw tooth regions 111 of the mold. As previously explained, even if it were to be possible to remove the main portion of one of the small strips, or the outer layer of one of them, by careful delamination of the paper, their edge portions are definitively fixed since they are totally integrated with the product.

Also as mentioned above, the saw tooth region could be located at any position on mold plate 106 that is superimposed, in the closed configuration of the mold, on the respective cavities 107, it being possible to have just one saw tooth region or a plurality of them associated with each cavity.

By the term "saw tooth" should be understood any roughened region of any pattern that permits perforation of the paper strip during injection, in the manner described above.

In practise it has been found that the use of roughened regions of a saw tooth nature facilitates perforation of the paper under the pressure of the plastic being injected, which then may penetrate the perforations thus formed and reach the other (outer) side of the paper without further damaging the paper. It will, however, be understood that other ways may be used for arriving at this important feature of this second preferred embodiment of the invention, that is to say, that a portion of the paper strip is covered by plastic on its face remote from cavity 107, such ways clearly being embraced by the generic concept of the invention.

What is claimed is:

1. A product made from injected plastic and having an identification surface to which a strip of paper printed with an individualized identification is permanently fixed, in which at least part of said identification surface has at least one protuberance covered by said strip of paper, to define at least one abrupt change in the plane of part of an outer surface of the strip of paper.

2. A product according to claim 1, wherein an inner surface of said strip of paper is integrated with the plastic of the product, including the region where it covers said protuberance.

3. A product according to claim 2, wherein said protuberance has a rectangular cross section.

4. A product according to claim 2, wherein there is a plurality of said protuberances.

5. A product according to claim 4, further comprising a security seal, and said identification surface being defined on an identification tab of said seal.

6. A product made from injected plastic and having an identification surface to which a strip of paper printed with an individualized identification is permanently fixed by having been applied at the time of injection of the plastic of which said product is made, wherein which at least part of an outer surface of said strip of paper is covered by the injected plastic of said product.

7. A product according to claim 6, wherein said at least part of an outer surface of said strip of paper is partially perforated by the injected plastic.

8. A product according to claim 7, wherein the covered part of said strip of paper is at the periphery of the strip.

9. A product according to claim 7, comprising a security seal, said identification surface being defined on an identification tab of said seal.

10. An injection mold for manufacturing the plastic product recited in claim 1 comprising first and second injection mold halves, said first mold half being formed with an injection cavity for forming part of said product to be personalized by solidifying the injected plastic with said printed strip of paper placed between said mold halves, and said second mold half closing said cavity in a closed configuration of the mold with said halves in mutual contact, wherein small reentrances are formed in the second mold half so as to permit that, at the time of injection of the plastic in the closed configuration of said mold, the plastic under pressure in said injection cavity deforms small regions of said strip of paper, forcing the deformed small regions into said small reentrances.

11. An injection mold according to claim 10, wherein said reentrances have a rectangular section in planes parallel to the surface of said second mold half.

12. An injection mold for manufacturing the plastic product recited in claim 6, comprising first and second injection mold halves, said first mold half being formed with an injection cavity for forming part of said product to be personalized by solidifying the injected plastic with said printed strip of paper placed between said mold halves, and said second mold half closing said cavity in a closed configuration of the mold with said halves in mutual contact, wherein said second mold half is shaped so as to permit the plastic, at the time of injection of the plastic in the closed configuration of said mold, to cover at least partially a side of the strip of paper that is remote from said mold cavity.

13. An injection mold according to claim 12, wherein said second mold half is shaped with at least one roughened region that is superimposed with respect to part of said injection cavity in the closed configuration of said mold.

14. An injection mold according to claim 13, wherein said roughened region has a saw tooth configuration to facilitate perforation of said strip of paper when an individualized product is manufactured by injecting plastic into said mold.

15. An injection mold according to claim 13, wherein there are two said roughened regions in said second mold half, located at positions corresponding to two opposite sides of the said injection cavity.

16. An injection mold according to claim 15, wherein each said roughened region extends along the complete length of the respective side of said injection cavity, in the closed configuration of said mold.

* * * * *